(12) United States Patent
Kwirandt

(10) Patent No.: US 8,624,972 B2
(45) Date of Patent: Jan. 7, 2014

(54) INSPECTION DEVICE FOR RECOGNIZING EMBOSSINGS AND/OR LABELS ON TRANSPARENT VESSELS, IN PARTICULAR BEVERAGE BOTTLES

(75) Inventor: Rainer Kwirandt, Barbing (DE)

(73) Assignee: Krones AG, Neutraubling (DE)

( * ) Notice: Subject to any disclaimer, the term of this patent is extended or adjusted under 35 U.S.C. 154(b) by 352 days.

(21) Appl. No.: 12/770,873

(22) Filed: Apr. 30, 2010

(65) Prior Publication Data
US 2010/0289892 A1 Nov. 18, 2010

(30) Foreign Application Priority Data
May 12, 2009 (DE) .................. 10 2009 020 920

(51) Int. Cl.
*H04N 7/18* (2006.01)

(52) U.S. Cl.
USPC ........................................................ 348/127

(58) Field of Classification Search
USPC ........................................................ 348/127
See application file for complete search history.

(56) References Cited

U.S. PATENT DOCUMENTS

| | | | |
|---|---|---|---|
| 4,376,951 A | 3/1983 | Miyazawa | |
| 5,004,909 A | 4/1991 | Fukuchi | |
| 6,304,323 B1 * | 10/2001 | Ishikura et al. | 356/239.4 |
| 6,320,641 B1 * | 11/2001 | Bauer et al. | 355/18 |
| 6,424,414 B1 | 7/2002 | Weiland et al. | |
| 2002/0093812 A1 * | 7/2002 | Kiest et al. | 362/33 |
| 2006/0037706 A1 * | 2/2006 | Putzer | 156/360 |
| 2008/0034628 A1 * | 2/2008 | Schnuckle | 40/310 |
| 2008/0037033 A1 * | 2/2008 | Ersue et al. | 356/604 |
| 2010/0141756 A1 * | 6/2010 | Grote et al. | 348/127 |

FOREIGN PATENT DOCUMENTS

| | | |
|---|---|---|
| CN | 1936496 B | 5/2010 |
| DE | 2938235 A1 | 4/1980 |
| DE | 68926362 T2 | 12/1996 |
| WO | WO-0151887 A1 | 7/2001 |
| WO | WO-2007136248 A1 | 11/2007 |

OTHER PUBLICATIONS

Robert Alexander Houstoun, "A treatise on light", 1919.*
Chinese Office Action for 201010178226.2, dated Jul. 20, 2012.
German Search Report for 10 2009 020 920.4, mailed Mar. 2, 2010.
Chinese Office Action for 201010178226.2 mailed Nov. 16, 2011.

* cited by examiner

*Primary Examiner* — Dave Czekaj
*Assistant Examiner* — Nam Pham
(74) *Attorney, Agent, or Firm* — Marshall, Gerstein & Borun LLP

(57) ABSTRACT

An inspection device and a method for recognizing embossings and/or labels on transparent vessels, in particular beverage bottles, and having a camera for imaging an embossing and a label of a vessel to be examined, and a transmitted light lamp provided with a luminescent screen and used for sending transmitted light through the embossing. In this way, a compact inspection device for recognizing labels and/or embossings and for examining their positions is provided.

10 Claims, 2 Drawing Sheets

INSPECTION DEVICE FOR RECOGNIZING EMBOSSINGS AND/OR LABELS ON TRANSPARENT VESSELS, IN PARTICULAR BEVERAGE BOTTLES

CROSS-REFERENCE TO RELATED APPLICATION

The present application claims the benefit of priority of German Application No. 102009020920.4, filed May 12, 2009. The entire text of the priority application is incorporated herein by reference in its entirety.

FIELD OF THE DISCLOSURE

The present disclosure relates to a method for recognizing embossings and/or labels on transparent vessels, in particular beverage bottles.

BACKGROUND

In beverage bottling processes, labels and relief-like impressions on bottles, so-called embossings, normally have to be aligned with respect to one another as accurately as possible. As is generally known, this is achieved in that, prior to being labeled, the filled bottles, which are positioned on rotatable centering devices, are brought into a defined initial rotary position; in so doing, the embossings are localized by forming a developed view of the bottle surface in front of a camera unit. However, the positioning of the bottles on the alignment cams of the centering devices as well as the drive means of the centering devices cause inaccuracies, so that it may perhaps not be possible to attach individual labels with the accuracy demanded.

Although known inspection devices for labels, like those described e.g. in DE 20 2005 020 478 U1, EP 0 872 724 A2 and U.S. Pat. No. 4,509,081, allow an imaging examination of the labels in incident light, the embossings, which have comparatively little contrast, cannot be recognized reliably by these devices.

SUMMARY OF THE DISCLOSURE

Hence, there is a demand for a compact, possibly retrofittable inspection device that can be used for recognizing labels and embossings and for examining their position relative to one another. It is an aspect of the present disclosure to provide such an inspection device.

This aspect is achieved with the aid of an inspection device comprising: a camera for imaging in a camera picture an embossing and/or a label of a vessel to be examined; and a transmitted light lamp provided with a luminescent screen and used for sending transmitted light through the embossing.

In transmitted light, embossings can be imaged with particularly high contrast. The illumination for recognizing embossings and labels can be optimized separately, so that a particularly precise and reliable evaluation of the camera picture will be possible.

The luminescent screen has preferably formed thereon areas with different luminous densities. This increases the contrast at the relief structures of the embossing in the camera picture, even if the embossings should not be very distinctive.

According to a particularly advantageous embodiment, there is a gradual change of luminous density between the areas of different luminous densities. This has the effect that brightness differences in areas having no relief structures can be eliminated particularly easily through filtering in the evaluation process, and relief structures in the camera picture can be localized more reliably and more precisely.

The areas of different luminous densities are preferably arranged in a strip pattern. This allows a generation of particularly distinctive contours in the camera picture.

According to a particularly advantageous embodiment, the strip pattern comprises one to three dark strips. This will especially improve the recognition of characters in the camera picture, e.g. the legibility of letters of the embossing.

The luminescent screen is preferably arranged outside the focal length of the vessel, so that the vessel acts as a cylindrical lens with respect to the transmitted light and the distance between the luminescent screen and the focal line of the vessel corresponds at most to twice the focal length of the vessel. A lamp having comparatively narrow dimensions will therefore suffice to produce the transmitted light. Hence, the device can be provided with a very compact structural design.

A particularly advantageous embodiment additionally comprises a computing unit for determining the position of the embossing and of the label in the camera picture. This allows a decision as to whether the bottle examined satisfies the quality requirements or whether it must be removed from the product stream.

According to a preferred embodiment, the inspection device additionally comprises an incident light lamp for illuminating the label with incident light. The label can thus be imaged with particularly high contrast and image sharpness.

According to a preferred embodiment, the brightness of the incident light lamp and/or of the transmitted light lamp can be adjusted such that the brightness difference between the embossing and the label in the camera picture becomes as small as possible. This will prevent the structures to be recognized from being overdriven in the camera picture or from being too dark or insufficiently contrasted for image evaluation with filtering and/or transformation.

The underlying object is additionally achieved with the aid of a method comprising: sending transmitted light through an embossing of a vessel to be examined; and imaging in a camera picture the embossing and/or a label of the vessel to be examined.

In transmitted light, embossings can be imaged with particularly high contrast. The illumination for recognizing embossings and labels can be optimized separately, so that a particularly precise and reliable evaluation of the camera picture will be possible.

According to a preferred embodiment of the method, the color spectrum of the transmitted light is adapted to the spectral transmission characteristics of the vessel and/or the vessel content. The brightness of the embossing in the camera picture can thus be increased.

The camera is preferably focused onto the front of the vessel and the aperture of the camera is opened to such an extent that an embossing arranged on the back of the vessel will be imaged fuzzily. A rear embossing can thus be removed by filtering the image data and, consequently, it can be differentiated from a sharply imaged embossing on the front of the vessel.

According to a particularly advantageous embodiment, the transmitted light is emitted by a luminescent screen, which is arranged outside the focal length of the vessel, so that the vessel acts as a cylindrical lens with respect to the transmitted light and the distance between the luminescent screen and the focal line of the vessel corresponds at most to twice the focal length of the vessel. A lamp having comparatively narrow dimensions will therefore suffice to produce the transmitted light. Hence, the inspection device can be provided with a particularly compact structural design.

According to a preferred embodiment, the method additionally comprises a step of illuminating the label with incident light. The label can thus be imaged with particularly high contrast and image sharpness.

The brightness of the incident light and/or of the transmitted light is preferably adjusted such that the brightness difference between the embossing and the label in the camera picture becomes as small as possible. This will prevent structures that are important for recognition from being overdriven or too dark in the camera picture. It follows that, after filtering and/or transformation, the associated image data can be evaluated in a suitable manner.

BRIEF DESCRIPTION OF THE DRAWINGS

A preferred embodiment of the present disclosure is shown in the drawing, in which.

DETAILED DESCRIPTION OF THE PREFERRED EMBODIMENT

Figure 1:
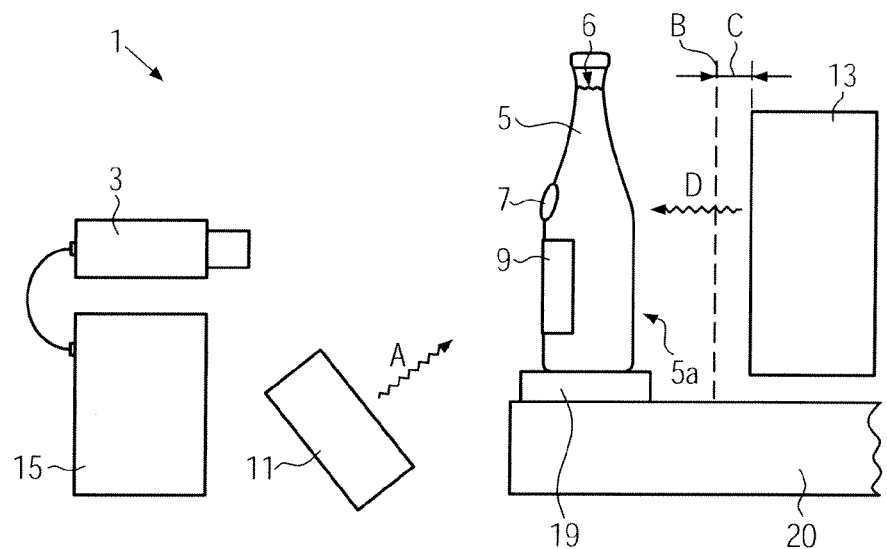
FIG. 1 shows a schematic side view of the inspection device.
Figure 2:
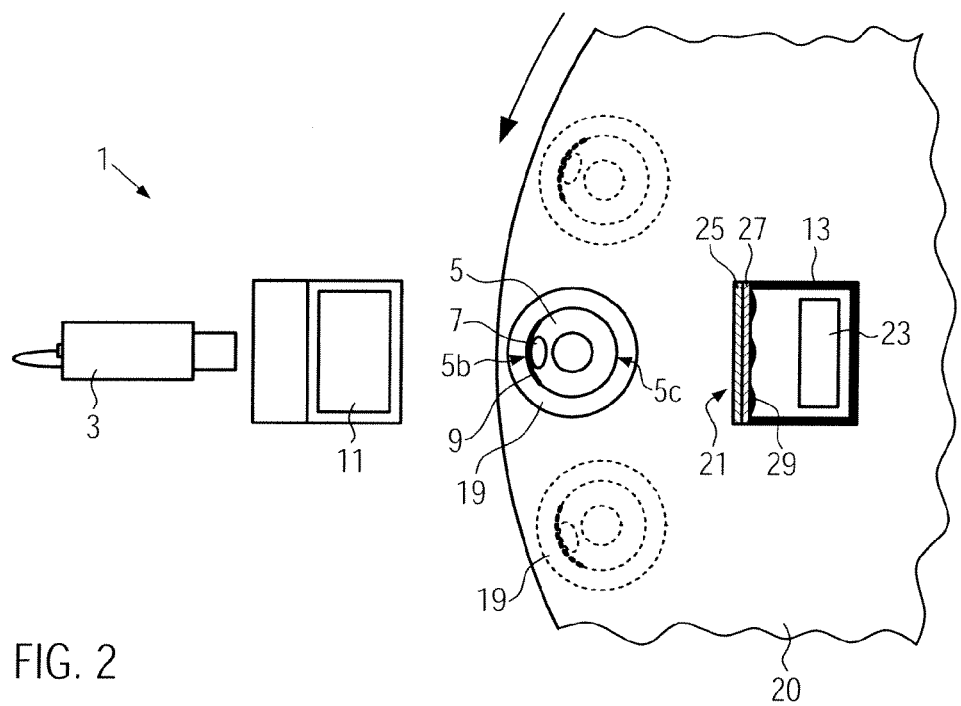
FIG. 2 shows a schematic top view of the inspection device.

As can be seen from FIGS. 1 and 2, the inspection device 1 according to the present disclosure comprises a camera 3 for imaging a transparent bottle 5 to be examined, said bottle 5 being provided with an embossing 7 and a label 9; an incident light lamp 11 directed onto the label 9; a transmitted light lamp 13 emitting light in the direction of the bottle 5 and the camera 3; and a computing unit 15 for evaluating camera pictures 17 taken with the camera 3. The figures additionally show centering holders 19 for the bottles 5, which are moved through the image area of the camera 3 on a conveying means 20, such as a conveying carousel or a conveying belt.

FIG. 2 shows the transmitted light lamp 13 provided with a luminescent screen 21 and a light source 23 in a sectional view. The luminescent screen 21 comprises, on the side facing the bottle 5, a diffusion disk 25, e.g. a frosted glass disk or a translucent plastic sheet, and, on the side facing the lamp 23, a sheet 27 which has printed thereon, section by section with different printing density, a dye 29. To make things clearer, the layer thickness of the dye 29 is highly exaggerated in FIG. 2; areas of large layer thickness correspond to areas of low luminous density and vice versa. The translucence of the dye 29 varies repeatedly in the horizontal direction along the luminescent screen 21 so that, as can be seen from FIG. 3, dark areas 31a having a low luminous density alternate with bright areas 31b having a high luminous density on the luminescent screen 21 in the horizontal direction. The luminous density of the dark areas 31a changes gradually into the luminous density of the bright areas 31b and vice versa.

Figure 3:
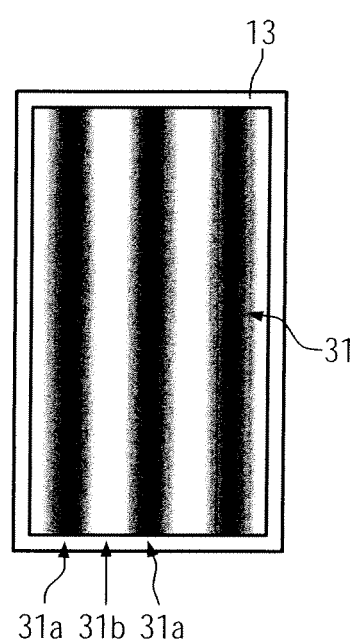
FIG. 3 shows a schematic front view of the transmitted light lamp according to FIGS. 1 and 2.

In particular the parallel perspective according to FIG. 3 shows clearly that the areas 31a,b of different luminous densities define on the luminescent screen 21 a strip pattern 31 which is oriented substantially vertically, i.e. parallel to the main axis of the bottle 5.

When such strip patterns 31 are used, minor beam deflections on the embossing 7 will already suffice to generate in the camera picture 17 sharply delimited, high-contrast structures which can consequently be identified reliably.

With respect to the beam path of the transmitted light, the bottle 5, in particular its cylindrical body 5a, acts as a biconvex cylindrical lens whose focal length can be calculated from the inner and outer bottle diameters as well as from the refractive indices of the bottle 5 and of the bottle content 6. The centering holder 19 and the transmitted light lamp 13 are arranged such that the distance C between the focal line B of the bottle 5 and the luminescent screen 21 is zero to twice the focal length of the cylindrical lens, preferably zero to once the focal length. This has the effect that, on the one hand, a sufficiently large distance is provided between the centering holder 19 and the transmitted light lamp 13; on the other hand, a transmitted light lamp 13 having comparatively narrow dimensions will, due to the magnifying effect of the cylindrical lens, already suffice to illuminate the whole width of the bottle 5. Depending on the design of the transmitted light lamp 13, the distance C may, however, also be larger. Likewise, the transmitted light lamp 13 could be arranged within the focal length of the bottle 5. In this case, the bottle 5 would, however, act as a magnifying glass and virtually image only a part of the luminescent screen 21.

The luminescent screen 21 comprises preferably one to five dark areas 31a; according to a particularly advantageous further development of the disclosure the number of dark areas 31a is three. Letters in the embossing 7 can thus be recognized particularly easily. The brightness transition on the imaged bottle 5 will be particularly advantageous for subsequent image evaluation, when the pattern 31 includes a central dark strip 31a. The device is, however, also imaginable with a larger number of dark areas 31a.

It is generally possible to provide other brightness distributions on the luminescent screen 21, e.g. strip patterns 31 having a substantially horizontal orientation, checker-board patterns or ring patterns, so that embossings 7 having a special shape can be recognized in a particularly reliable manner.

The gradual transition of the luminous density from the areas 31a to the areas 31b and vice versa corresponds preferably to a wavy pattern, e.g. a sinusoid.

The sheet 27 can have printed thereon the dye 29 on an arbitrary side thereof or on both sides thereof. Likewise, it is possible to incorporate the dye 29 in the sheet 27. It is also imaginable to apply, e.g. by means of screen printing, the dye 29 directly to the side of the diffusion disk 25 facing the light source 23. The use of a sheet 27 offers, however, the advantage that various strip patterns 31 can be exchanged easily, so as to adapt the inspection device 1 to specific bottle shapes and/or structures on the bottle surface.

It will be expedient when the dye 29 has primarily an optical absorption effect so as to form the areas 31a having a low luminous density. It would, however, also be possible to form the areas 31b having a high luminous density with the aid of a fluorescent dye 29. The areas 31a,b may also be formed by a combination of absorbing and/or fluorescent dyes 29.

Alternatively, the dark and bright areas 31a,b may also be produced by illuminating the luminescent screen 21 areawise with different brightnesses. To this end, the light source 23 may be implemented as an LED matrix whose LED elements emit light with different intensities. Depending on the number and size of the elements, said elements would have to be arranged at a suitable distance from the diffusion disk 25 so that a smoothed illumination pattern 31 with gradual brightness transitions is defined. By means of this variant, different patterns 31 could also be produced without converting the device.

The light source 23 is preferably a pulsed LED lamp with adjustable brightness and pulse length or a flash lamp with adjustable flash duration. Other types of lamps are, however, imaginable as well. The emission spectrum of the transmitted light lamp 13 is preferably adapted to the absorption spectrum of the bottle 5 and/or of the bottle content 6, so as to transmit light through the embossing 7 as efficiently as possible and so as to brightly represent the embossing in the camera picture 17.

The incident light lamp 11 is a pulsed LED lamp with adjustable brightness and pulse length or a flash lamp with adjustable flash duration. Other types of lamps are, however, imaginable as well.

The brightness and/or the pulse length of the incident light lamp 11 and of the transmitted light lamp 13 are preferably adjusted such that the embossing 7 and the label 9 can be localized in the same camera picture 17 by means of pattern or character recognition, i.e. the embossing 7 and the label 9 are illuminated such that their brightnesses will, as far as possible, be identical in the camera picture 17 or lie within a suitable dynamic range that can be resolved by the camera 3. Such a brightness adaptation of e.g. the incident light lamp 11 could also be accomplished by a filter, e.g. a neutral density filter, in the illumination beam path. A direct adjustment of the lamp brightness or of the pulse length should, however, be preferred with respect to the amount of energy consumed and in view of the higher flexibility in the case of a change of product.

The camera 3 is focused on the front 5b of the bottle 5 facing the camera 3 and records an image of said front 5b preferably with the stop open, i.e. with a minimum depth of field. In this way, it is accomplished that an embossing 7 located on the back 5c of the bottle 5 facing way from the camera 3 is imaged fuzzily and can therefore reliably be differentiated from an embossing 7 on the front 5b. The fuzzily imaged embossing 7 causes soft brightness transitions in the camera picture 17, which can be eliminated in said camera picture 17 by suitable filtering during evaluation. It is thus possible to recognize a bottle 5 to which the label 9 has, by mistake, been applied such that it is offset by 180° relative to the embossing 7.

In the case of sharp imaging with a suitably reduced aperture of the camera, a rear embossing 7 could, alternatively, also be recognized in that it is horizontally widened by the cylindrical lens-effect of the bottle 5 and imaged in a laterally reversed fashion in the camera picture 17.

The computing unit 15 evaluates the camera pictures 17 by filtering with edge and/or bandpass filters and/or Fourier transformation and by subsequent pattern or character recognition. In the course of this process, the pattern 31 of the transmitted light lamp 13 increases the contrast in the imaged raised portions and depressions of the embossing 7, whereas in the remaining areas of the imaged bottle 5 the pattern 31 is removed by the filtering or transformation due to the gradual brightness transitions between the bright and dark areas 31a, b. This allows a localization of the embossing 7 with high reliability and accuracy.

The inspection device 1 is suitable for examining the position of the embossing 7 or the position of the label 9 with respect to the embossing 7 at a predetermined rotary position of the bottle 5; during inspection, the bottle 5 may be rotated or it may stand still.

It would, however, also be possible to localize the embossing 7 and/or a burr of the bottle 5 in transmitted light D in the case of an unknown rotary position of the bottle, so as to be able to move the bottle to a predetermined rotary position before a label is attached thereto. Embossing recognition in transmitted light D can, for example, serve as a position indicator for aligning a burr, an embossing, etc., for future or subsequent labeling. In this case, the incident light lamp 11 can be dispensed with.

For such an inspection of a rotating, unlabelled bottle 5, the transmitted light lamp 13 should be provided with a larger width, since a larger number of camera pictures 17 of the bottle 5 moving past the transmitted light lamp 13 on the conveying means 20 will then have to be taken at various rotary positions. In this case, it may also be necessary to provide a plurality of cameras 3 with laterally overlapping image areas.

Although it is advantageous to use the incident light lamp 11 for imaging the label 9, since this will allow a bright and reproducible illumination of the label and, consequently, short exposure times, imaging of the label 9 would, in principle, also be possible without the above-described incident light lamp 11, with the aid of other light sources, such as ambient light.

The bottle 5 is e.g. a beverage bottle consisting of glass or PET. The inspection device 1 can, however, be used for examining arbitrary transparent containers provided with a label and an embossing, even when the respective containers should be empty.

The inspection device can be employed as follows: a product stream consisting of labeled bottles 5 is moved by the conveying means 20 through the image area of the camera 3. Prior to inspection, the bottles 5 are brought into a predetermined rotary position with the centering holder 19 so that the labels 9 to be examined are directed towards the camera 3.

During inspection, the centering holder 19 may be rotated or it may stand still. In the image area of the camera 3, the label 9 is illuminated by the incident light lamp 11, e.g. by a flash of light A. At the same time, the transmitted light lamp 13 transmits light, preferably by means of a flash of light D, through the bottle 5 from the side facing away from the camera. The camera 3 takes a picture 17 of the bottle 5 illuminated in the incident light A and in the transmitted light D, the brightness and the flash duration of the lamps 11, 13 being adapted to one another such that the embossing 7 and the label 9 will appear in the camera picture 17 with brightnesses which are identical, as far as possible. The image data are transmitted to a computing unit 15, which extracts, by means of filtering and/or Fourier transformation, the patterns that are suitable for position recognition. This step is facilitated and rendered more precise by the fact that the transmitted light D is generated by a luminescent screen 21 with a strip-shaped, gradual brightness distribution. This improves the contrast of the relief structures of the embossing 7 and suppresses artifacts in areas outside of these relief structures. Making use of pattern or character recognition, the positions of the embossing 7 and of the label 9 are detected and compared with one another. If the embossing 7 and/or the label 9 do/does not lie within a predetermined tolerance range, the bottle 5 can be removed from the product stream.

The invention claimed is:

1. An inspection device for examining the positions of embossings and labels relative to another, on transparent vessels, in particular beverage bottles, comprising:
   a camera for imaging in a camera picture an embossing and a label of a vessel to be examined;
   a transmitted light lamp provided with a luminescent screen and used for sending light through the embossing to image the embossing in transmitted light at the same time the label is illuminated with incident light, wherein the luminescent screen has formed thereon areas with different luminous densities, wherein there is a gradual change of luminous density between the areas of different luminous densities, the inspection device further comprising a computing unit for determining the position of the embossing and of the label in the camera picture; and an incident light lamp for illuminating the label to image the label in the incident light.

2. An inspection device according to claim 1, wherein the areas of different luminous densities are arranged in a strip pattern.

3. An inspection device according to claim 2, wherein the strip pattern comprises one to three dark strips.

4. An inspection device according to claim 1, wherein the luminescent screen is arranged outside the focal length of the vessel, so that the vessel acts as a cylindrical lens with respect to the light from the luminescent screen and the distance between the luminescent screen and the focal line of the vessel corresponds at most to twice the focal length of the vessel.

5. An inspection device according to claim 1, wherein the brightness of the incident light lamp and/or of the transmitted light lamp can be adjusted such that the brightness difference between the embossing and the label in the camera picture becomes as small as possible.

6. A method of examining the positions of embossings and labels relative to another, on transparent vessels, in particular beverage bottles, comprising:

a) sending light from a luminescent screen having formed thereon areas with different luminous densities, wherein there is a gradual change of luminous density between the areas of different luminous densities, through an embossing of a vessel to be examined;

b) illuminating a label of the vessel to image the label in incident light during during sending of the light from the luminescent screen through the embossing, wherein the incident light and the light from the luminescent screen are from different light sources;

c) imaging in a camera picture the embossing and the label of the vessel to be examined; and d) determining the position of the embossing and of the label, based on the camera picture.

7. A method according to claim 6, and adapting the color spectrum of the light from the luminescent screen to the spectral transmission characteristics of the vessel and/or vessel content so as to transmit light through the embossing as efficiently as possible.

8. A method according to claim 6, and focusing the camera onto the front of the vessel and opening the aperture of the camera to such an extent that an embossing arranged on the back of the vessel is imaged fuzzily.

9. A method according to claim 6, and emitting the light from a luminescent screen, which is arranged outside the focal length of the vessel, so that the vessel acts as a cylindrical lens with respect to the emitted light and the distance between the luminescent screen and the focal line of the vessel corresponds at most to twice the focal length of the vessel.

10. A method according to claim 6, and adjusting the brightness of the incident light and/or of the light transmitted through the embossing such that the brightness difference between the embossing and the label in the camera picture becomes as small as possible.

* * * * *